US00PP17147P2

(12) United States Plant Patent
Danziger

(10) Patent No.: US PP17,147 P2
(45) Date of Patent: Oct. 10, 2006

(54) ***SUTERA* PLANT NAMED 'DANCOPINKEYE'**

(50) Latin Name: ***Sutera* sp.**
Varietal Denomination: Dancopinkeye

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/138,293

(22) Filed: May 27, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Wendy Haas
(74) *Attorney, Agent, or Firm*—Foley & Lardner LLP

(57) ABSTRACT

A new and distinct *Sutera* plant named 'Dancopinkeye' characterized by having 5-petalled purple colored flowers with a purple halo around the throat measuring 1.5 cm in diameter; trailing vigorous growth; early flowering response; suitable for use with hanging baskets, combination planters and ground cover under full sunlight or slight shade; and good weather tolerance.

2 Drawing Sheets

Botanical designation: *Sutera* sp.
Variety denomination: 'Dancopinkeye'.

BACKGROUND OF THE INVENTION

The present invention relates to a new and distinct cultivar of *Sutera* plant, botanically known as *Sutera* sp., hereinafter referred to by the cultivar name 'Dancopinkeye'.

*Sutera*, of the Scrophulriaceae family, consists of annuals which are grown in most climate zones in the U.S., and only in zones 9 and 10 if it is a perennial plant.

The new *Sutera* cultivar is a product of a planned breeding program conducted by the inventor, Gabriel Danziger, in Moshav Mishmar Hashiva, Israel. The objective of the breeding program was to develop a new *Sutera* variety with large, purple flowers with a purple halo around the throat and compact, trailing growth habit.

The new *Sutera* cultivar originated from open pollination in a controlled breeding program by the inventor in 2003 in Moshav Mishmar Hashiva, Israel. The female parent is an *Sutera* cultivar designated as 'CV-03-53' (unpatented). The male parent is unknown. The new *Sutera* cultivar 'Dancopinkeye' was discovered and selected by the inventor, Gabriel Danziger, as a flowering plant within the progeny of the stated cross in a controlled environment in Moshav Mishmar Hashiva, Israel.

'Dancopinkeye' was selected in a cultivated environment in Moshav Mishmar Hashiva, Israel. Asexual reproduction of the new *Sutera* cultivar by vegetative cuttings was first performed in July of 2003 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Dancopinkeye' which in combination distinguish this *Sutera* as a new and distinct cultivar:

1. 5-petalled purple colored flowers with a purple halo around the throat measuring 1.5 cm in diameter;
2. Trailing vigorous growth;
3. Early flowering response;
4. Suitable for use with hanging baskets, combination planters and ground cover under full sunlight or slight shade; and
5. Good weather tolerance.

Plants of 'Dancopinkeye' differ from the plants of the female parent, 'CV-03-53' (unpatented) primarily in flower color and growth habit. The flower color of 'Dancopinkeye' is darker purple than the parent. 'Dancopinkeye' flowers are purple, RHS 76 B, with a purple halo, RHS 76 A, around the throat, whereas 'CV-03-53' flowers are purple, RHS 76 D, and have no halo. Plants of 'Dancopinkeye' have more compact growth habit than plants of 'CV-03-53'.

Of the many commercial cultivars known to the present inventor, the most similar in comparison to 'Dancopinkeye' is the *Sutera* cultivar 'Copia Lavender' (unpatented). The new cultivar 'Dancopinkeye' is distinguishable from 'Copia Lavender' in flower color. The flower color of 'Dancopinkeye' is purple, RHS 76 B, with a purple halo, RHS 76 A, around the throat, whereas 'Copia Lavender' flowers are violet-blue, RHS 91 B.

BRIEF DESCRIPTION OF THE DRAWINGS

The accompanying photographic drawings illustrate the overall appearance of the new *Sutera* cultivar 'Dancopinkeye' showing the colors as true as is reasonably possible with colored reproductions of this type. Colors in the photographs may differ slightly from the color value cited in the detailed botanical description which accurately describe the color of 'Dancopinkeye'.

The first photograph shows a side view perspective of a typical 'Dancopinkeye' plant in a hanging basket at 3 months.

The second photograph shows a close-up of a single flower of 'Dancopinkeye' at 3 months.

DETAILED BOTANICAL DESCRIPTION

'Dancopinkeye' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sutera* cultivar as grown in a greenhouse in Moshav Mishmar Hashiva, Israel, under conditions which closely approximate those generally used in commercial practice.

Color references are made to The Royal Horticultural Society Colour Chart (R.H.S.), 2001 edition, except where general colors of ordinary significance are used. Color values were taken under daylight conditions at approximately 12:00 noon in Moshav Mishmar Hashiva, Israel. The age of the plant described is 2 months.

Classification:
- *Botanical.*—*Sutera* sp.
- *Commercial.*—*Sutera* cv. Copia Pink Touch.

Parentage:
- *Female parent.*—*Sutera* cultivar designated 'CV-03-53' (unpatented).
- *Male parent.*—Open pollination.

Propagation: Tip cuttings of side shoots.

Growing conditions:
- *Light intensities.*—Full sunlight or slight shade.
- *Temperature.*—During day: Range of 20° C. to 24° C. During night: Range of 16° C. to 20° C.
- *Tolerance.*—Tolerant to low and high temperatures.
- *Fertilization.*—A balanced fertilizer with level of 100 ppm Nitrogen.
- *Growth regulators.*—Not necessary.

Plant:
- *General appearance and form.*—Height: About 6 cm. Spread: About 42 cm.
- *Shape.*—Trailing.
- *Winter hardiness.*—Hardy in moderate climate.
- *Vigor.*—Strong.
- *Rooting habit and description.*—Easy to root.
- *Time to initiate roots.*—7 to 10 days.
- *Time to produce a rooted cutting.*—14 days.
- *Branching habit.*—Vigorously branched.
- *Lateral branches.*—

TABLE 1

| Branch Characteristic | Primary | Secondary |
|---|---|---|
| Length | 39 cm. | 8 cm. |
| Diameter | 2 mm. | 1 mm. |
| Internode Length | 3 cm. | 2 cm. |
| Texture | Slightly rough | Slightly rough |
| Pubescence | Yes | Yes |
| Color | Green, RHS 139C | Green, RHS 139C |

- *Crop time.*—8 to 10 weeks for a flowering pot.
- *Fragrance.*—None.

Foliage:
- *Overall shape of leaf.*—Rhomboidal.
- *Base shape.*—Acuminate.
- *Apex shape.*—Acute.
- *Margin.*—Dentate.
- *Texture.*—Slightly velvety.
- *Pubescence.*—Slightly velvety.
- *Leaf length.*—About 2.5 cm.
- *Leaf width.*—About 1.5 cm.
- *Color of upper surface.*—Mature leaf: Yellow-Green, RHS 147A. Immature leaf: Green, RHS 137A.
- *Color of lower surface.*—Mature leaf: Green, RHS 137A. Immature leaf: Yellow-Green, RHS 146A.
- *Venation color.*—Upper surface: Yellow-Green, RHS 147A. Lower surface: Green, RHS 137A.
- *Petiole.*—Length: 10 mm. Diameter: 1 mm. Color: Yellow-Green, RHS 147A.

Flower description:
- *Natural flowering season.*—All year round in moderate climate.
- *Lastingness of the bloom.*—Flowering of a single flower lasts for 7 days.
- *Quantity of flowers and buds per plant.*—About 200.
- *Flower size.*—Diameter (spread): About 15 mm. Diameter at lobes: About 15 mm. Diameter of corolla tube: About 2 mm. Overall flower height: About 8 mm.
- *Flower bud.*—Height: About 8 mm. Diameter: About 5 mm. Color: Purple, RHS 76B. Shape: Spatulas.
- *Petals.*—Shape: Oval. Length: About 5 mm. Width: About 5 mm. Apex: Truncate. Margin: Entire. Texture: Slightly velvety. Color: Upper surface, when opening: Purple, RHS 76B, with Halo, Purple, RHS 76A. Upper surface, opened flower: Purple, RHS 76B, with Halo, Purple, RHS 76A. Lower surface, when opening: Purple, RHS 76C. Lower surface, opened flower: Purple, RHS 76C.
- *Corolla throat color.*—Yellow-Orange, RHS 17A.
- *Calyx.*—Appearance: Deeply 5 lobed.
- *Sepals.*—Quantity: 5. Shape: Linear. Apex: Acute. Base: Fused. Margin: Entire. Length: About 5 mm. Diameter: About 2 mm. Upper surface color: Green, RHS 137B. Lower surface color: Green, RHS 137B.
- *Pedicel.*—Aspect: Slanted upward. Length: About 10 mm. Diameter: About 1 mm. Angle: 45°. Color: Green, RHS 138A.

Reproductive organs:
- *Stamen.*—Number: 4. Color: Green-Yellow, RHS 1A.
- *Anthers.*—Color: Yellow, RHS 12A. Shape and length: Cylinder, About 1 mm.
- *Pollen.*—Color: Yellow, RHS 12A.
- *Pistils.*—Quantity: 1. Length: About 8 mm.
- *Stigma.*—Shape: Undulate. Color: Green-Yellow, RHS 1A.
- *Ovary.*—Color: Green, RHS 143C.

Seeds:
- *Width.*—About 0.5 mm.
- *Length.*—About 1 mm.
- *Shape.*—Elliptic.
- *Texture.*—Warty.
- *Color.*—Greyed-Orange, RHS 164B.

Fruit:
- *Width.*—About 2.5 mm.
- *Length.*—About 5.5 mm.
- *Shape.*—Ellipsoid.
- *Texture.*—Warty.
- *Color.*—Greyed-Orange, RHS 165B.

Disease resistance: No information is currently available.

Disease susceptibility: No information is currently available.

I claim:

1. A new and distinct *Sutera* plant named 'Dancopinkeye', substantially as illustrated and described herein.

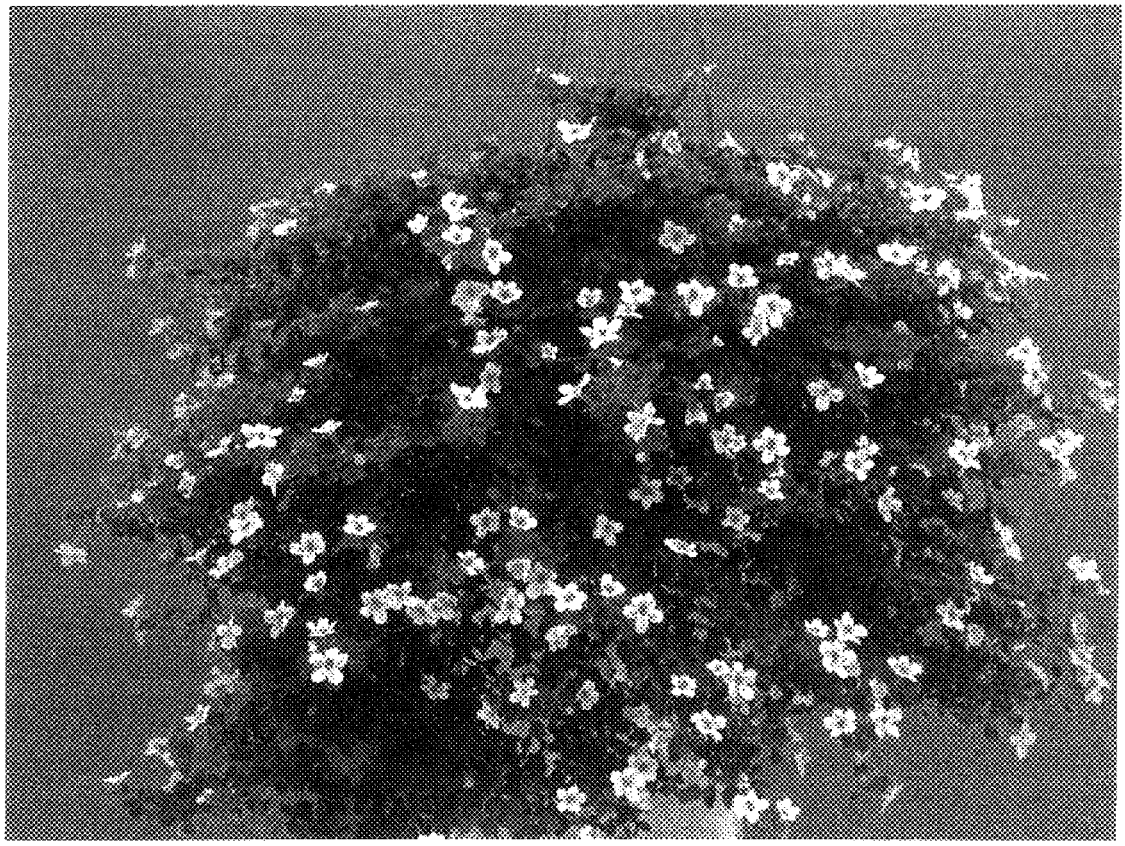

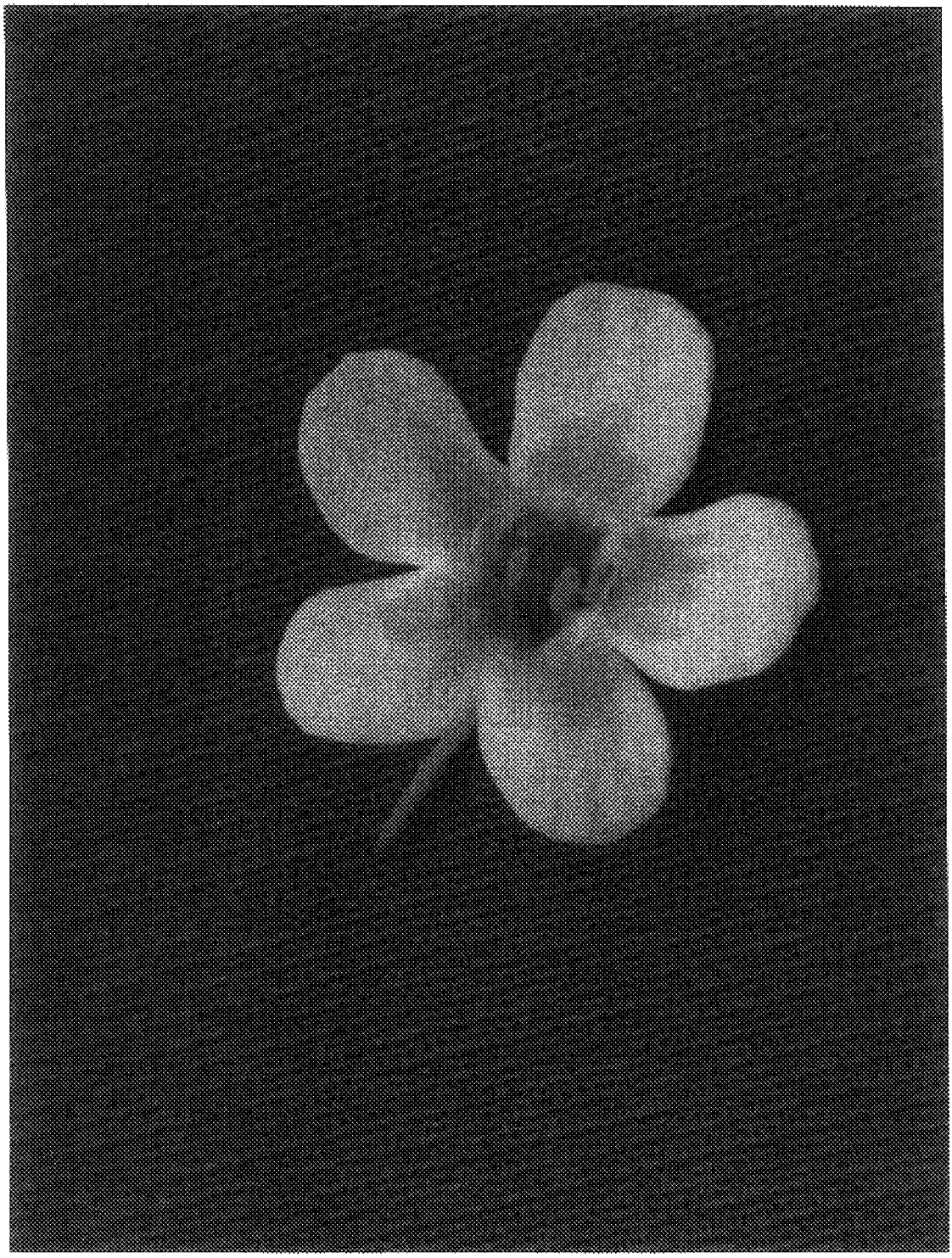

* * * * *